(12) United States Patent
Oh

(10) Patent No.: US 10,475,698 B2
(45) Date of Patent: Nov. 12, 2019

(54) AMBIPOLAR TRANSISTOR AND ELECTRONIC SENSOR OF HIGH SENSITIVITY USING THE SAME

(71) Applicant: Teresa Oh, Cheongju-si (KR)

(72) Inventor: Teresa Oh, Cheongju-si (KR)

( * ) Notice: Subject to any disclaimer, the term of this patent is extended or adjusted under 35 U.S.C. 154(b) by 124 days.

(21) Appl. No.: 15/475,544

(22) Filed: Mar. 31, 2017

(65) Prior Publication Data

US 2018/0286969 A1   Oct. 4, 2018

(51) Int. Cl.
| | |
|---|---|
| *H01L 21/00* | (2006.01) |
| *H01L 29/00* | (2006.01) |
| *H01L 21/765* | (2006.01) |
| *H01L 29/40* | (2006.01) |
| *G01N 27/414* | (2006.01) |

(52) U.S. Cl.
CPC ......... *H01L 21/765* (2013.01); *G01N 27/414* (2013.01); *H01L 29/408* (2013.01)

(58) Field of Classification Search
CPC ............. H01L 29/7393; H01L 29/4908; H01L 29/408; H01L 29/0847; H01L 29/51; H01L 29/78684; H01L 29/7869; H01L 21/765; H01L 21/02118; H01L 21/02126; H01L 21/28273; H01L 27/283; H01L 27/0259; H01L 27/0288; H01L 27/281; G01J 1/44; G01N 27/414
See application file for complete search history.

(56) References Cited

U.S. PATENT DOCUMENTS

| | | | | |
|---|---|---|---|---|
| 6,828,951 | B2* | 12/2004 | Yamazaki | G09G 3/3233 345/77 |
| 7,750,339 | B2* | 7/2010 | Setayesh | B82Y 10/00 257/347 |
| 9,935,187 | B1* | 4/2018 | Oh | H01L 29/4908 |
| 2006/0163561 | A1* | 7/2006 | Setayesh | B82Y 10/00 257/40 |
| 2011/0163679 | A1* | 7/2011 | Chiang | H05B 33/0809 315/185 R |

OTHER PUBLICATIONS

Oh et al., "Study on Characteristic Properties of Annealed SiOC Film Prepared by Inductively Coupled Plasma Chemical Vapor Deposition", 2010,IEEE Transactions on Plasma Science, vol. 38 No. 7 pp. 1598-1602 (Jul. 2010). (Year: 2010).*

\* cited by examiner

*Primary Examiner* — Nikolay K Yushin
(74) *Attorney, Agent, or Firm* — Kile Park Reed & Houtteman PLLC

(57) ABSTRACT

Disclosed are an ambipolar transistor and a high-sensitivity electronic sensor using the same. The ambipolar transistor includes: a substrate; a gate formed on the substrate; a gate insulating film formed of an SiOC thin film and disposed on the substrate and the gate; and a source portion and a drain portion formed on the gate insulating film and spaced apart from each other, wherein the source portion and the drain portion comprise: a main source terminal and a main drain terminal disposed on the gate insulating film at right and left sides of the gate, respectively; and a plurality of source sub-terminals and a plurality of drain sub-terminals alternately arranged between the main source terminal and the main drain terminal, respectively.

3 Claims, 6 Drawing Sheets

AMBIPOLAR TRANSISTOR AND ELECTRONIC SENSOR OF HIGH SENSITIVITY USING THE SAME

TECHNICAL FIELD

The present invention relates to an ambipolar transistor and a high-sensitivity electronic sensor using the same, and more particularly, to an ambipolar transistor with negative resistance using a leakage current cutoff insulating film, a high-sensitivity electronic sensor using fine diffusion current, and a method of fabricating the same.

BACKGROUND

As harmful elements propagated through the air such as fine dust, avian influenza, foot-and-mouth disease, MERS, mycobacteria, and the like cause serious problems, there has been a growing interest in eco-friendliness and increasing demand for a portable living environment measuring instrument. Therefore, there is a need for a high-sensitivity sensor.

In a typical semiconductor sensor, an electrode and a sensor material are formed in close contact with each other on a substrate and a heater is attached under the substrate to increase sensitivity. When the sensor material is in close contact with the electrode, there can be problems of increase in resistance and generation of leakage current. In addition, because of the need for the heater, there is a limit to reducing the size of the sensor, and a separate constant-voltage circuit breaker for preventing discharge is required due to overcurrent generated by the heater. Further, there is also a problem with a battery that operates such a system.

A separate embedded system for amplifying a current sensed by a sensory receptor, which is the sensor material, blocking leakage current, and converting signals is used to increase sensitivity. However, such a system has the disadvantage of amplifying noise.

Since such typical sensors are always accompanied by a problem of leakage current, there is a need for technology capable of preventing leakage current.

In sensory receptor-based electrochemical and photochemical sensors or biosensors, there are problems of deterioration in reliability and reduction in electrical sensitivity due to increase in contact resistance and generation of leakage current during conversion of measured currents into electrical signals.

Although sensor technology using graphene with high electron transfer speed has been applied, the problem of leakage current has not been solved. In order to apply the sensor technology, it is necessary to comprehensively consider detection limit, selectivity, and device.

Typical sensor technology has a problem in that it is impossible to measure particles having a size of 300 mm or less, only the concentration of mass can be measured, it is difficult to measure in real time, and sensor products are expensive. MEMS-based semiconductor sensors have low resolution due to the occurrence of minute leakage current and have lower sensitivity than photochemical sensors and thus are difficult to combine with IoT-based digital smart communication technology in view of low threshold voltage shift and mobility of transistors.

In addition, since ultra-fine dust real-time sensing technology using MEMS-based particle chips requires lots of processes such as dust collecting/filtering, ultrafine dust sorting and charging, ultrafine dust collecting, and conversion of water concentration through measurement of ultra-fine dust current so as to increase sensitivity, there can be problem of deterioration in reliability.

BRIEF SUMMARY

Some embodiments of the present invention provide a transistor which uses diffusion current flowing in a thin insulating film to increase sensitivity of a semiconductor sensor, and a high-sensitivity electronic sensor using the same.

In accordance with one embodiment of the present invention, an ambipolar transistor includes: a substrate; a gate formed on the substrate; a gate insulating film formed of an SiOC thin film and disposed on the substrate and the gate; and a source portion and a drain portion formed on the gate insulating film and spaced apart from each other, wherein the source portion and the drain portion includes: a main source terminal and a main drain terminal disposed on the gate insulating film at right and left sides of the gate, respectively; and a plurality of source sub-terminals and a plurality of drain sub-terminals alternately arranged between the main source terminal and the main drain terminal, respectively.

The plurality of source sub-terminals and the plurality of drain sub-terminals may be alternately arranged to be separated from each other and connected to each other in series between the main source terminal and the main drain terminal.

The gate insulating film may have an allowable dielectric constant of 0.1 to 2.5.

The gate insulating film may have an allowable leakage current of $10^{-14}$ A to $10^{-10}$ A.

A bias applied to the drain portion may range from $10^{-4}$ V to 1 V.

In accordance with another embodiment of the present invention, an ambipolar transistor includes: a substrate; a gate connected to the substrate; an SiOC insulating film formed on the substrate; an interlayer electrode formed on the SiOC insulating film; an SiOC insulating film formed on the interlayer electrode; and a source portion and a drain portion formed on the SiOC insulating film and spaced apart from each other, wherein the SiOC insulating film and the interlayer electrode are alternately stacked one above another, and wherein the source portion and the drain portion include: a main source terminal and a main drain terminal disposed at right and left sides of the SiOC insulating film, respectively; and a plurality of source sub-terminals and a plurality of drain sub-terminals arranged between the main source terminal and the main drain terminal, respectively.

The gate may be formed in the SiOC insulating film formed on the substrate.

The gate may be formed at an edge of the substrate outside the SiOC insulating film.

The gate may be formed under the substrate.

The plurality of source sub-terminals and the plurality of drain sub-terminals may be alternately arranged to be separated from each other and connected to each other in series between the main source terminal and the main drain terminal.

The gate insulating film may have an allowable dielectric constant of 0.1 to 2.5.

The interlayer electrode may be formed of any one selected from aluminum (Al), nanowire, graphene, ITO, transparent conductive oxide (TCO), AZO, ZTO, IGZO, ZITO, SiZO, hybrid (composite), and CNT-based transparent electrodes.

In accordance with a further embodiment of the present invention, a high-sensitivity electronic sensor using an ambipolar transistor includes: a sensor part connected to a gate; a power source connected to a drain terminal; and a display connected to a source terminal, wherein diffusion current between the source terminal and the drain terminal allows reception of electrical signals, and the ambipolar transistor including the gate, the drain terminal, and the source terminal includes: a substrate; a gate formed on the substrate; a gate insulating film formed of an SiOC thin film and disposed on the substrate and the gate; and a source portion and a drain portion formed on the gate insulating film and spaced apart from each other, wherein the source portion and the drain portion includes: a main source terminal and a main drain terminal disposed on the gate insulating film at right and left sides of the gate, respectively; and a plurality of source sub-terminals and a plurality of drain sub-terminals arranged between the main source terminal and the main drain terminal, respectively.

The ambipolar transistor may include: a substrate; a gate connected to the substrate; an SiOC insulating film formed on the substrate; an interlayer electrode formed on the SiOC insulating film; an SiOC insulating film formed on the interlayer electrode; and a source portion and a drain portion formed on the SiOC insulating film and spaced apart from each other, wherein the SiOC insulating film and the interlayer electrode are alternately stacked one above another, and wherein the source portion and the drain portion include: a main source terminal and a main drain terminal disposed at right and left sides of the SiOC insulating film, respectively; and a plurality of source sub-terminals and a plurality of drain sub-terminals arranged between the main source terminal and the main drain terminal, respectively.

A variable resistor for controlling sensitivity may be located in front of the sensor part connected to the gate.

The power source connected to the drain terminal may be an AC power source including a Wheatstone bridge.

According to the present invention, it is possible to provide a high-sensitivity electronic sensor which can measure the concentration of particles in ppm, provide real-time measurement, and is cost-effective in mass production.

According to the present invention, it is possible to provide a transistor which includes source and drain signal lines arranged to be connected to each other in series on a gate insulating film to amplify electrical signals, thereby improving sensitivity of an electronic sensor while blocking leakage current using diffusion current.

According to the present invention, it is possible to provide a transistor which allows design of a nanometer scale circuit while preventing leakage current using diffusion current, thereby sensing signals in the THz range and generating electrical signals.

BRIEF DESCRIPTION OF THE DRAWINGS

The above and other aspects, features and advantages of the present invention will become apparent from the following description of embodiments given in conjunction with the accompanying drawings, in which.

DETAILED DESCRIPTION

Figure 1:
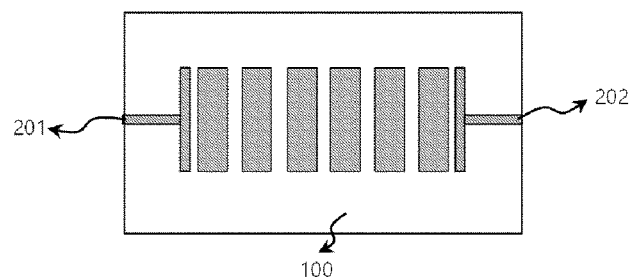
FIG. 1 is a top view of a series pattern diffusion current transistor according to a first embodiment of the present invention.

Hereinafter, embodiments of the present invention will be described in detail with reference to the accompanying drawings.

The present invention relates to a transistor structure required for generating an electrical signal suitable for a high-sensitivity sensor, and more particularly, to an ambipolar transistor which can overcome the problem that a transistor without a channel layer is difficult to put to practical use due to very low current value, and a high-sensitivity electronic sensor using the same.

A typical transistor has a structure in which a source terminal is separated from a drain terminal by a gate and a gate insulating film and a channel is formed between the source and drain terminals. In addition, change of a current value is mainly controllable by the channel. Thus, in such a transistor, the source terminal and the drain terminal cannot be arranged to have series or parallel connection.

In a transistor without a channel layer, diffusion current is generated by spontaneous polarization caused by a potential difference due to a potential barrier created by a depletion layer or an amorphous insulating film. Dielectrics exhibit spontaneous polarization. Thus, due to transfer characteristics of diffusion current, when a negative (−) voltage is applied to an SiOC insulating film as a gate insulating film, a positive (+) diffusion current flows on the opposite side, and when a positive (+) voltage is applied to the SiOC insulating film, a negative (−) diffusion current flows on the opposite side. Therefore, when the SiOC thin film is used as the gate insulating film, it is possible to obtain a transistor capable of having ambipolar transfer characteristics depending on the position of a gate.

Such a diffusion current generated due to spontaneous polarization of the dielectrics acts in a direction opposite the direction of a drift current and thus can reduce the internal potential difference. Thus, when the SiOC insulating film is disposed at a metal/semiconductor interface, which can cause increase in resistance due to metal contact, due to spontaneous polarization of dielectrics having a low dielectric constant, a potential barrier caused by the insulating film generates a diffusion current acting in a direction opposite the direction of a drift current, thereby allowing much current to flow through the metal contact by preventing increase in resistance due to metal contact.

Thus, when an insulating material having physicochemically and electrically stable properties comparable to a depletion layer is used, a diffusion current can be stably generated, such that a transistor having ambipolar transfer characteristics can be easily produced into a high-sensitivity electronic sensor.

As an insulating film having such characteristics, an SiOC thin film is a next-generation insulating thin film having excellent insulating properties and stable physicochemical characteristics, and thus can easily form Schottky contact with a potential barrier due to low polarization to minimize the contact resistance at the interface to allow more diffusion current to flow, thereby increasing efficiency of an electronic sensor.

Hereinafter, embodiments of a transistor capable of generating diffusion current using a SiOC gate insulating film and an electronic sensor using the same will be described in detail with reference to the accompanying drawings.

Figure 2:
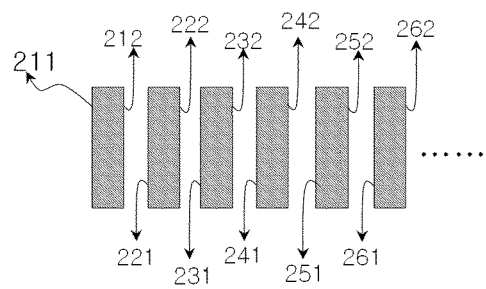
FIG. 2 is a view of a source-drain terminal pattern of the series pattern diffusion current transistor of FIG. 1.
Figure 3:
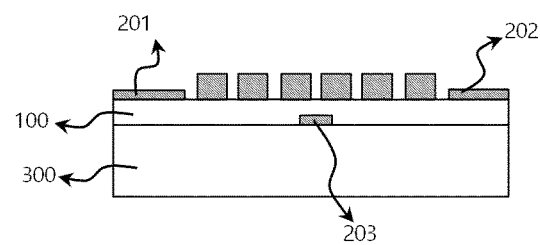
FIG. 3 is a sectional view of the series pattern diffusion current transistor of FIG. 1.

FIG. 1 is a top view of a series pattern diffusion current transistor according to a first embodiment of the present invention, FIG. 2 is a view of a source-drain terminal pattern of the series pattern diffusion current transistor of FIG. 1, and FIG. 3 is a sectional view of the series pattern diffusion current transistor of FIG. 1.

Referring to FIGS. 1 to 3, an ambipolar transistor using diffusion current according to a first embodiment of the present invention includes: a gate 203 formed on a substrate 300; a gate insulating film 100 formed on the substrate 300 and the gate 203 and formed of a SiOC thin film; and a source portion and a drain portion formed on the gate insulating layer 100 and spaced apart from each other.

In addition, when drain and source signal lines are disposed on the gate insulating film 100, in order to amplify electrical signals (voltage) while increasing sensitivity, the source portion and the drain portion may include: a main source terminal 202 and a main drain terminal 201; and a plurality of source sub-terminals and a plurality of drain sub-terminals, respectively, wherein the plurality of source sub-terminals 212, 222, 232, . . . and the plurality of drain sub-terminals 211, 221, 231, . . . are each formed of a metal wire and are alternately arranged to be connected to each other in series.

The transistor according to the present invention has a structure in which the main source terminal 202 and the main drain terminal 201 are stacked on the gate insulating film 100 without a channel layer, unlike a typical transistor having a channel layer. Here, the gate insulating film 100 is formed of a SiOC thin film and preferably has a dielectric constant of 1.0 to 2.5.

Further, in order for an electronic sensor fabricated using the transistor to have high sensitivity, the gate insulating film 100 has a leakage current of $10^{-14}$ A to $10^{-10}$ A and is required to be amorphous instead of exhibiting polarization.

The SiOC thin film used as the gate insulating film of the transistor according to the present invention may be formed by a process in which an SiOC target is deposited by sputtering, ICP-CVD, or PE-CVD, followed by heat treatment.

In order to reduce polarization of the SiOC film, that is, to inhibit increase in polarization due to carbon and oxygen, the carbon content is controlled. When the carbon content of the SiOC target is 0.1% or less, it is difficult to form the SiOC thin film. Preferably, the carbon content of the SiOC target ranges from 0.05% to 15% so as to restrict the dielectric constant of the gate insulating film 100 to a range of 1.0 to 2.5.

Figure 4:
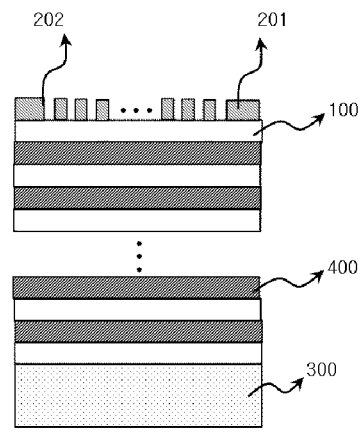
FIG. 4 is a sectional view of a series pattern diffusion current transistor according to a second embodiment of the present invention.
Figure 5:
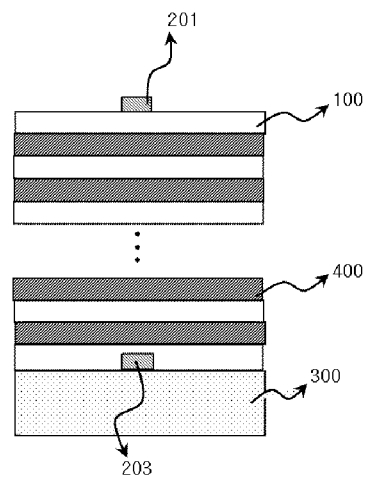
FIG. 5 is a sectional view of a series pattern diffusion current transistor according to a third embodiment of the present invention.
Figure 6:
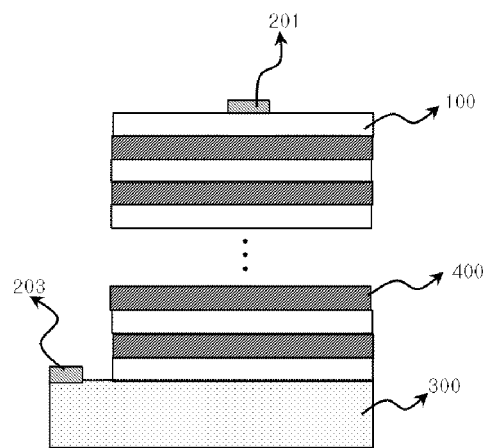
FIG. 6 is a sectional view of a series pattern diffusion current transistor according to a fourth embodiment of the present invention.
Figure 7:
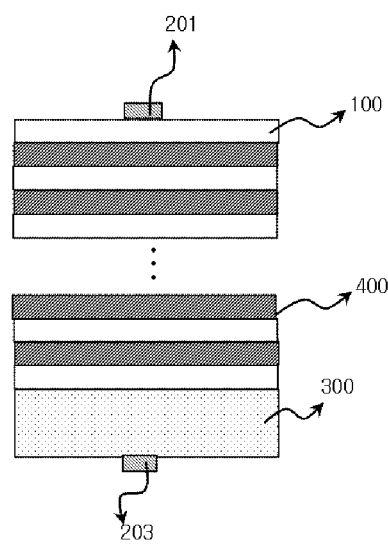
FIG. 7 is a sectional view of a series pattern diffusion current transistor according to a fifth embodiment of the present invention.

FIG. 4 is a sectional view of a series pattern diffusion current transistor according to a second embodiment of the present invention, FIG. 5 is a sectional view of a series pattern diffusion current transistor according to a third embodiment of the present invention, FIG. 6 is a sectional view of a series pattern diffusion current transistor according to a fourth embodiment of the present invention, and FIG. 7 is a sectional view of a series pattern diffusion current transistor according to a fifth embodiment of the present invention.

An ambipolar transistor using diffusion current according to a second embodiment of the present invention includes a gate 203 connected to a substrate 300, an interlayer electrode 400 formed on the substrate, an SiOC insulating film 100 formed on the interlayer electrode 400, and a source portion and a drain portion formed on the interlayer electrode and spaced apart from each other, wherein the interlayer electrode and the SiOC insulating film 100 include a plurality of interlayer electrodes and a plurality of SiOC insulating films alternately stacked one above another, respectively.

In addition, the source portion and the drain portion include: a main source terminal 202 and a main drain terminal 201 disposed at right and left sides of the SiOC insulating film 100, respectively; and a plurality of source sub-terminals and a plurality of drain sub-terminals, respectively, wherein the plurality of source sub-terminals 212, 222, 232, . . . and the plurality of drain sub-terminals 211, 221, 231, . . . are each formed of a metal wire and are alternately arranged to be connected to each other in series.

As in the first embodiment, the SiOC thin film 100 preferably has a dielectric constant of 1.0 to 2.5 and a leakage current of $10^{-14}$ A to $10^{-10}$ A, and is required to be amorphous instead of exhibiting polarization.

FIG. 5 is a sectional view of a series pattern diffusion current transistor according to a third embodiment of the present invention. In this embodiment, the gate is formed in the SiOC insulating film 100 and on the substrate.

FIG. 6 is a sectional view of a series pattern diffusion current transistor according to a fourth embodiment of the present invention. In this embodiment, the gate is formed at an edge of the substrate outside the SiOC insulating film.

FIG. 7 is a sectional view of a series pattern diffusion current transistor according to a fifth embodiment of the present invention. In this embodiment, the gate is formed under the substrate.

In the ambipolar diffusion current transistors according to the second to fifth embodiments, the interlayer electrode 400 may be formed of any one selected from aluminum (Al), nanowire, graphene, ITO, transparent conductive oxide (TCO), AZO, ZTO, IGZO, ZITO, SiZO, hybrid (composite), and CNT-based transparent electrodes.

In the ambipolar diffusion current transistors according to the second to fifth embodiments, the interlayer electrode 400 is stacked on the substrate 300, the SiOC insulating film 100 is stacked on the interlayer electrode, and the plurality of source terminals and the plurality of drain terminals are alternately arranged to be connected to each other in series between the main drain terminal 201 and the main source terminal 202.

Figure 8:
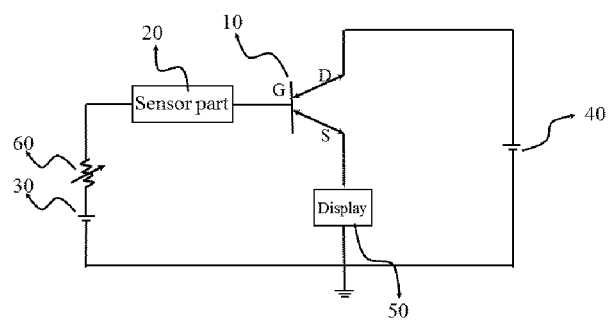
FIG. 8 is a DC circuit diagram of a high-sensitivity electronic sensor using the ambipolar transistor according to the embodiments of the present invention.

FIG. 8 is a DC circuit diagram of a high-sensitivity electronic sensor using the ambipolar transistor according to the embodiments of the present invention.

Referring to FIG. 8, the high-sensitivity electronic sensor using the ambipolar transistor includes: a sensor part 20 and a gate power source 30a connected to a gate G; a drain power source 40 connected to a drain terminal D; and a display connected to a source terminal, wherein diffusion current between the source terminal and the drain terminal allows reception of electrical signals. Here, the ambipolar transistor 10 including the gate, the drain terminal, and the source terminal may be any one of the ambipolar transistors as shown in FIGS. 1 to 7.

An electronic sensor using the ambipolar transistor according to the first embodiment as shown in FIG. 1 includes: a gate 203 formed on a substrate 300; a gate insulating film 100 formed on the substrate 300 and the gate and formed of a SiOC thin film; and a source portion and a drain portion formed on the gate insulating film 100 and spaced apart from each other.

When drain and source signal lines are disposed on the gate insulating film 100, in order to amplify electrical signals (voltage) while increasing sensitivity, the source portion and the drain portion may include: a main source terminal 202 and a main drain terminal 201; and a plurality of source sub-terminals and a plurality of drain sub-terminals, respectively, wherein the plurality of source sub-terminals 212, 222, 232, . . . and the plurality of drain sub-terminals 211, 221, 231, . . . are alternately arranged to be connected to each other in series.

An electronic sensor using the ambipolar transistor according to the second embodiment as shown in FIG. 2 includes: a gate 203 connected to a substrate 300; an interlayer electrode 400 formed on the substrate; an SiOC insulating film 100 formed on the interlayer electrode 400; and a source portion and a drain portion formed on the SiOC insulating film and spaced apart from each other, wherein the interlayer electrode and the SiOC insulating film 100 include a plurality of interlayer electrodes and a plurality of SiOC insulating films alternately stacked one above another, respectively.

In addition, the source portion and the drain portion include: a main source terminal 202 and a main drain terminal 201 disposed at right and left sides of the SiOC insulating film 100, respectively; and a plurality of source sub-terminals and a plurality of drain sub-terminals, respectively, wherein the plurality of source sub-terminals 212, 222, 232, . . . and the plurality of drain sub-terminals 211, 221, 231, . . . are each formed of a metal wire and are alternately arranged to be connected to each other in series.

FIG. 8 is a circuit diagram of an electronic sensor having a DC power source. In the electronic sensor, a sensor part 20 is connected to a gate and diffusion current between source and drain terminals allows reception of electrical signals. In addition, the sensor part is separated from a signal transmission unit, thereby increasing reliability. Further, since diffusion current is used, there is no leakage current, such that sensitivity can be increased, and a differential amplifier for blocking noise and amplifying a signal is not required.

Referring to FIG. 8 again, a variable resistor 60 for controlling sensitivity is connected to the power source 30 to be located in front of the sensor part 20 connected to the gate; another power supply 40 is connected to the drain terminal; and the source terminal is connected to a display.

Figure 9:
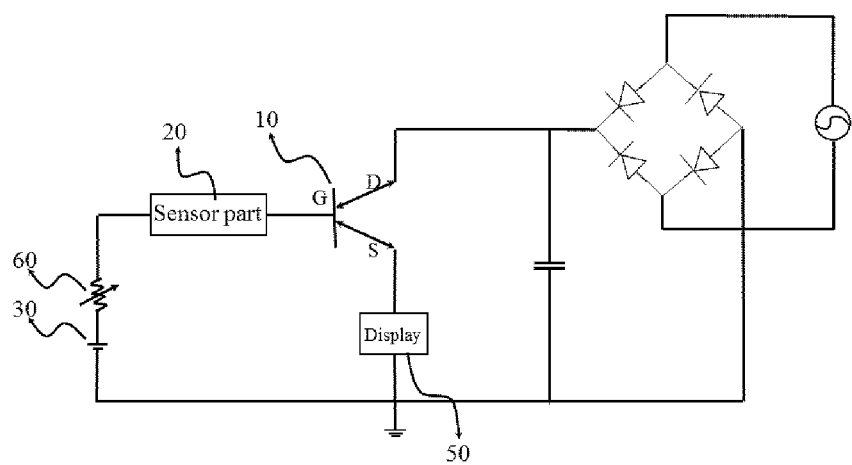
FIG. 9 is an AC circuit diagram of a high-sensitivity electronic sensor using the ambipolar transistor according to the embodiments of the present invention.

FIG. 9 is an AC circuit diagram of a high-sensitivity electronic sensor using the ambipolar transistor according to the embodiments of the present invention.

Referring to FIG. 9, in the high-sensitivity electronic sensor according to this embodiment, an AC power source 90 including a Wheatstone bridge is connected to the drain terminal.

In this embodiment, even when a high voltage is applied, the sensor can be driven by a diffusion current generated therein to prevent overvoltage and current leakage, thereby increasing lifespan of an electronic device.

Figure 10:
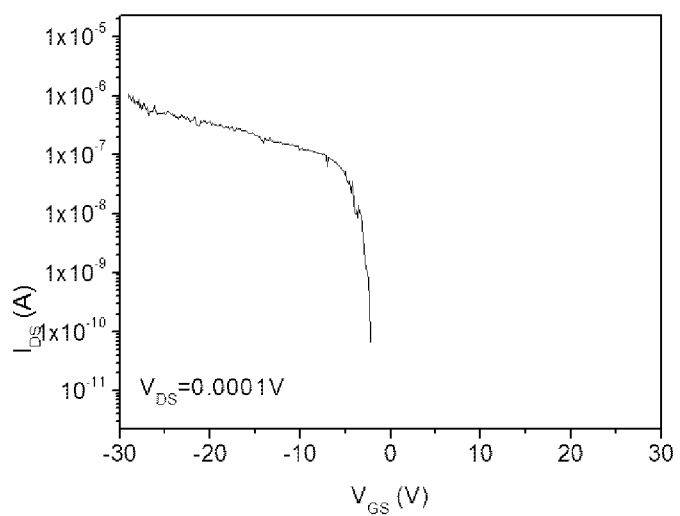
FIG. 10 is a graph depicting transfer characteristics of an ambipolar transistor using a single layer of a gate insulating film.
Figure 11:
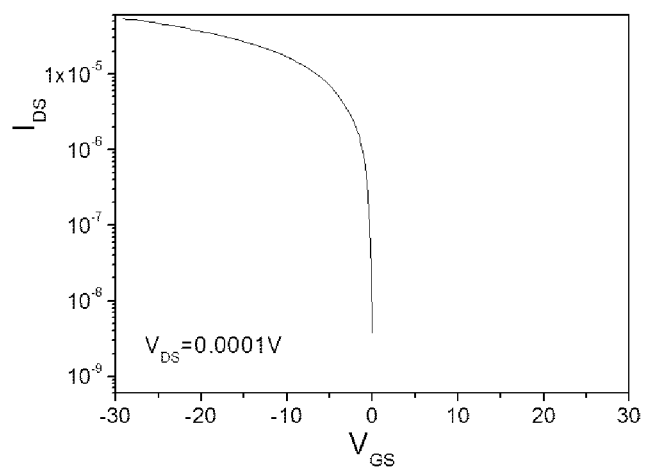
FIG. 11 is a graph depicting transfer characteristics of the series pattern diffusion current transistor according to the present invention.

FIG. 10 is a graph depicting transfer characteristics of an ambipolar transistor using a single layer of a gate insulating film; FIG. 11 is a graph depicting transfer characteristics of the series pattern diffusion current transistor according to the present invention; and FIG. 12 is a graph depicting the transfer characteristics of the series pattern diffusion current transistor of FIG. 11 on a log scale.

As shown in FIG. 10, it can be seen that a very low current of about $-10^{-6}$ A flows through the ambipolar transistor using the single layer of the gate insulating film. Conversely, as shown in FIG. 11, it can be seen that the current value is increased to $-10^{-4}$ A due to the influence of a series pattern in the series pattern diffusion current transistor.

In addition, linear characteristics of $I_{DS}$-$V_{GS}$ transfer characteristics of the series connection-type transistor according to the first embodiment exhibit ambipolarity. That is, when a gate voltage is redirected from the negative direction to the positive direction, a drain current is redirected from the positive direction to the negative direction. Since the gate insulating film 100 can induce tunneling of a diffusion current due to spontaneous polarization of an amorphous dielectric, when a negative bias is applied to the gate 203, a (+) source-drain current flows through the thin film transistor, whereas when a positive bias is applied to the gate, a (−) source-drain current flows through the transistor.

Figure 12:
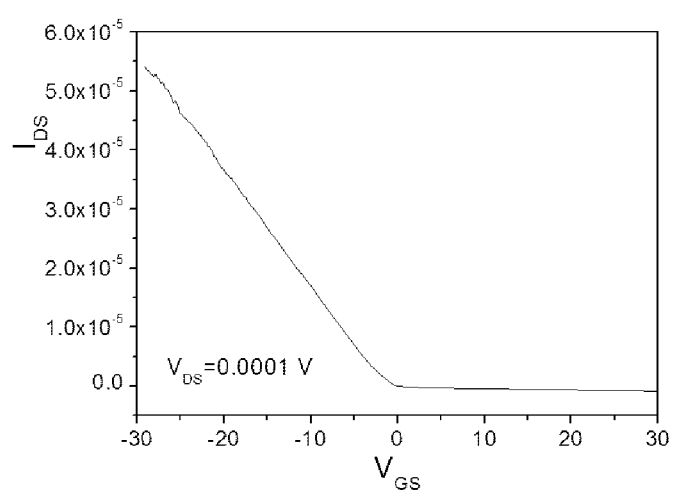
FIG. 12 is a graph depicting the transfer characteristics of the series pattern diffusion current transistor of FIG. 11 on a log scale.

FIG. 12 is a graph depicting mobility and on/off characteristics acquired by converting the IDS-VGS transfer characteristics of FIG. 11 into a log scale. As shown in FIG. 12, it can be seen that the stability and mobility of the transfer characteristics increase with decreasing drain voltage.

Referring to FIG. 12, as the drain voltage decreases, tunneling of minority carriers at an interface between a semiconductor and the gate insulating film can be more easily achieved. Preferably, a bias applied to the drain ranges from $10^{-4}$ V to 1 V.

Although some embodiments have been disclosed above, it should be understood that these embodiments are given by way of illustration only, and that various modifications, variations, and alterations can be made without departing from the spirit and scope of the present invention. Therefore, the scope of the present invention should be limited only by the accompanying claims and equivalents thereof.

What is claimed is:

1. A high-sensitivity electronic sensor using an ambipolar transistor, comprising:
   a sensor part connected to a gate;
   a power source connected to a drain terminal;
   a display connected to a source terminal; and
   a variable resistor for controlling sensitivity is located in front of the sensor part connected to the gate,
   wherein diffusion current between the source terminal and the drain terminal allows reception of electrical signals, and
   the ambipolar transistor comprises:
   a substrate;
   the gate formed on the substrate;
   a gate insulating film formed of an SiOC thin film and disposed on the substrate and the gate; and
   a source portion and a drain portion formed on the gate insulating film and spaced apart from each other,
   wherein the source portion and the drain portion comprise: a main source terminal and a main drain terminal disposed on the gate insulating film at right and left sides of the gate, respectively; and a plurality of source sub-terminals and a plurality of drain sub-terminals arranged between the main source terminal and the main drain terminal, respectively.

2. The high-sensitivity electronic sensor according to claim 1, wherein the power source connected to the drain terminal is an AC power source comprising a Wheatstone bridge.

3. A high-sensitivity electronic sensor using an ambipolar transistor, comprising:
   a sensor part connected to a gate;
   a power source connected to a drain terminal;
   a display connected to a source terminal; and
   a variable resistor for controlling sensitivity is located in front of the sensor part connected to the gate,
   wherein diffusion current between the source terminal and the drain terminal allows reception of electrical signals, and
   the ambipolar transistor comprises:

a substrate;
the t-gate connected to the substrate;
a first SiOC insulating film formed on the substrate;
an interlayer electrode formed on the first SiOC insulating film;
a second SiOC insulating film formed on the interlayer electrode; and
a source portion and a drain portion formed on the second SiOC insulating film and spaced apart from each other, and
wherein the source portion and the drain portion comprise: a main source terminal and a main drain terminal disposed at right and left sides of the second SiOC insulating film, respectively; and a plurality of source sub-terminals and a plurality of drain sub-terminals arranged between the main source terminal and the main drain terminal, respectively.

* * * * *